(12) United States Patent
Truschel et al.

(10) Patent No.: US 9,775,558 B2
(45) Date of Patent: Oct. 3, 2017

(54) SYSTEMS AND METHODS FOR TREATING SLEEP APNEA

(75) Inventors: William A. Truschel, Oakmont, PA (US); Anandi Mahadevan, Monroeville, PA (US); Christopher Anthony Procyk, New Kensington, PA (US); Mark Christopher McDermott, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 429 days.

(21) Appl. No.: 14/005,389

(22) PCT Filed: Mar. 13, 2012

(86) PCT No.: PCT/IB2012/051165
§ 371 (c)(1),
(2), (4) Date: Sep. 16, 2013

(87) PCT Pub. No.: WO2012/127358
PCT Pub. Date: Sep. 27, 2012

(65) Prior Publication Data
US 2014/0000611 A1    Jan. 2, 2014

Related U.S. Application Data

(60) Provisional application No. 61/454,605, filed on Mar. 21, 2011.

(51) Int. Cl.
*F16K 31/02*    (2006.01)
*A61B 5/00*    (2006.01)
(Continued)

(52) U.S. Cl.
CPC ............ *A61B 5/4836* (2013.01); *A61B 5/085* (2013.01); *A61B 5/087* (2013.01); *A61B 5/0826* (2013.01);
(Continued)

(58) Field of Classification Search
CPC .............. A61M 16/0069; A61M 16/00; A61M 16/204–16/205; A61M 2016/0042;
(Continued)

(56) References Cited

U.S. PATENT DOCUMENTS

| 5,546,933 A * | 8/1996 | Rapoport | A61B 5/0002 |
| | | | 128/204.21 |
| 5,803,066 A | 9/1998 | Rapoport | |
| 6,257,234 B1 * | 7/2001 | Sun | A61M 16/0051 |
| | | | 128/204.18 |

FOREIGN PATENT DOCUMENTS

| EP | 0373585 A1 | 6/1990 |
| JP | 2000504602 A | 4/2000 |

(Continued)

OTHER PUBLICATIONS

Lorx A. et al., "Low-FFrequency Assessment of Airway and Tissue Mechanics in Ventilated COPD Patients", Journal of Applied Physiology, vol. 107, No. 6, Dec. 1, 2009 (Dec. 1, 2009), pp. 1884-1892, XP55030627.

*Primary Examiner* — Todd J Scherbel
*Assistant Examiner* — Victoria Leszczak
(74) *Attorney, Agent, or Firm* — Michael W. Haas

(57) ABSTRACT

Sleep apnea can be treated using positive airway pressure. Methods and systems for determining a level of airway obstruction allow beneficial adjustments to the level of expiratory positive airway pressure used to treat a subject.

9 Claims, 5 Drawing Sheets

(51) Int. Cl.
*A61B 5/085* (2006.01)
*A61B 5/087* (2006.01)
*A61F 5/56* (2006.01)
*A61M 16/00* (2006.01)
*A61B 5/08* (2006.01)
*A61M 16/16* (2006.01)
*A61M 16/10* (2006.01)

(52) U.S. Cl.
CPC ............... *A61F 5/56* (2013.01); *A61M 16/00* (2013.01); *A61M 16/0006* (2014.02); *A61M 16/0051* (2013.01); *A61M 16/0069* (2014.02); *A61M 16/10* (2013.01); *A61M 16/161* (2014.02); *A61B 5/4818* (2013.01); *A61M 2016/0021* (2013.01); *A61M 2016/0027* (2013.01); *A61M 2016/0039* (2013.01); *A61M 2016/102* (2013.01); *A61M 2205/3365* (2013.01); *A61M 2205/3368* (2013.01); *A61M 2205/3375* (2013.01); *A61M 2205/505* (2013.01); *A61M 2205/52* (2013.01); *A61M 2230/46* (2013.01)

(58) Field of Classification Search
CPC .......... A61M 2205/52; A61M 2230/40; A61M 2205/3331; A61B 5/085; A61B 5/4818; A61B 5/0002; A61B 5/0816; A61B 5/08; A61B 5/7282
See application file for complete search history.

(56) References Cited

FOREIGN PATENT DOCUMENTS

| WO | WO0010634 A1 | 3/2000 | |
| WO | WO 2010070497 A1 * | 6/2010 | ............ A61M 16/00 |
| WO | WO2010070497 A1 | 6/2010 | |

* cited by examiner

SYSTEMS AND METHODS FOR TREATING SLEEP APNEA

This patent application claims the priority benefit under 35 U.S.C. §371 of international patent application no. PCT/IB2012/051165, filed Mar. 13, 2012, which claims the priority benefit under 35 U.S.C. §119(e) of U.S. Provisional Application No. 61/454,605 filed on Mar. 21, 2011, the contents of which are herein incorporated by reference.

BACKGROUND OF THE INVENTION

1. Field of the Invention

The present disclosure pertains to systems and methods for treating sleep apnea, and, in particular, treating obstructive sleep apnea while enhancing expiratory positive airway pressure support.

2. Description of the Related Art

Obstructive sleep apnea is a condition in which a subject (e.g. a patient) experiences episodes of obstructed breathing during sleep, either due to an obstructed airway and/or a collapsed airway. This condition may e.g. occur when the muscles in the upper throat of a subject relax during sleep. Existing treatments include using expiratory positive airway pressure (EPAP) support, e.g. via an EPAP device. Practical limitations of EPAP devices include discomfort for the subject, and, in certain operating conditions, inability to maintain open airways for the subject.

SUMMARY OF THE INVENTION

Accordingly, it is an object of one or more embodiments of the present disclosure to provide a system for treating sleep apnea in a subject having a collapsible or obstructed airway while enhancing expiratory positive airway pressure. The system includes a pressure generator configured to generate a pressurized flow of breathable gas for delivery to the airway of the subject; one or more sensors configured to generate one or more output signals conveying measurements related to one or more breathing parameters and/or mechanical airway parameter of the subject, a control module, a resistance module, and an adjustment module. The control module is configured to control the pressure generator to adjust one or more parameters of the pressurized flow of breathable gas such that the airway of the subject is provided with a target expiratory positive airway pressure. The resistance module is configured to estimate upper airway resistance of the subject based on the one or more output signals from one or more sensors. The adjustment module is configured to adjust the target expiratory positive airway pressure based on the estimations of upper airway resistance.

It is yet another aspect of one or more embodiments of the present disclosure to provide a method of treating sleep apnea in a subject having a collapsible or obstructed airway while enhancing expiratory positive airway pressure. The method includes delivering a pressurized flow of breathable gas having a target expiratory positive airway pressure to the airway of the subject; generating one or more output signals conveying measurements related to one or more breathing parameters and/or mechanical airway parameters of the subject; estimating upper airway resistance of the subject based on the one or more output signals and adjusting the target expiratory positive airway pressure based on the estimations of upper airway resistance.

It is yet another aspect of one or more embodiments to provide a system configured to treat sleep apnea in a subject having a collapsible or obstructed airway while enhancing expiratory positive airway pressure. The system includes a means for delivering a pressurized flow of breathable gas having a target expiratory positive airway pressure to the airway of the subject; a means for generating one or more output signals conveying measurements related to one or more breathing parameters and/or mechanical airway parameters of the subject; a means for estimating upper airway resistance of the subject based on one or more output signals; and a means for adjusting the target expiratory positive airway pressure based on the estimations of upper airway resistance.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
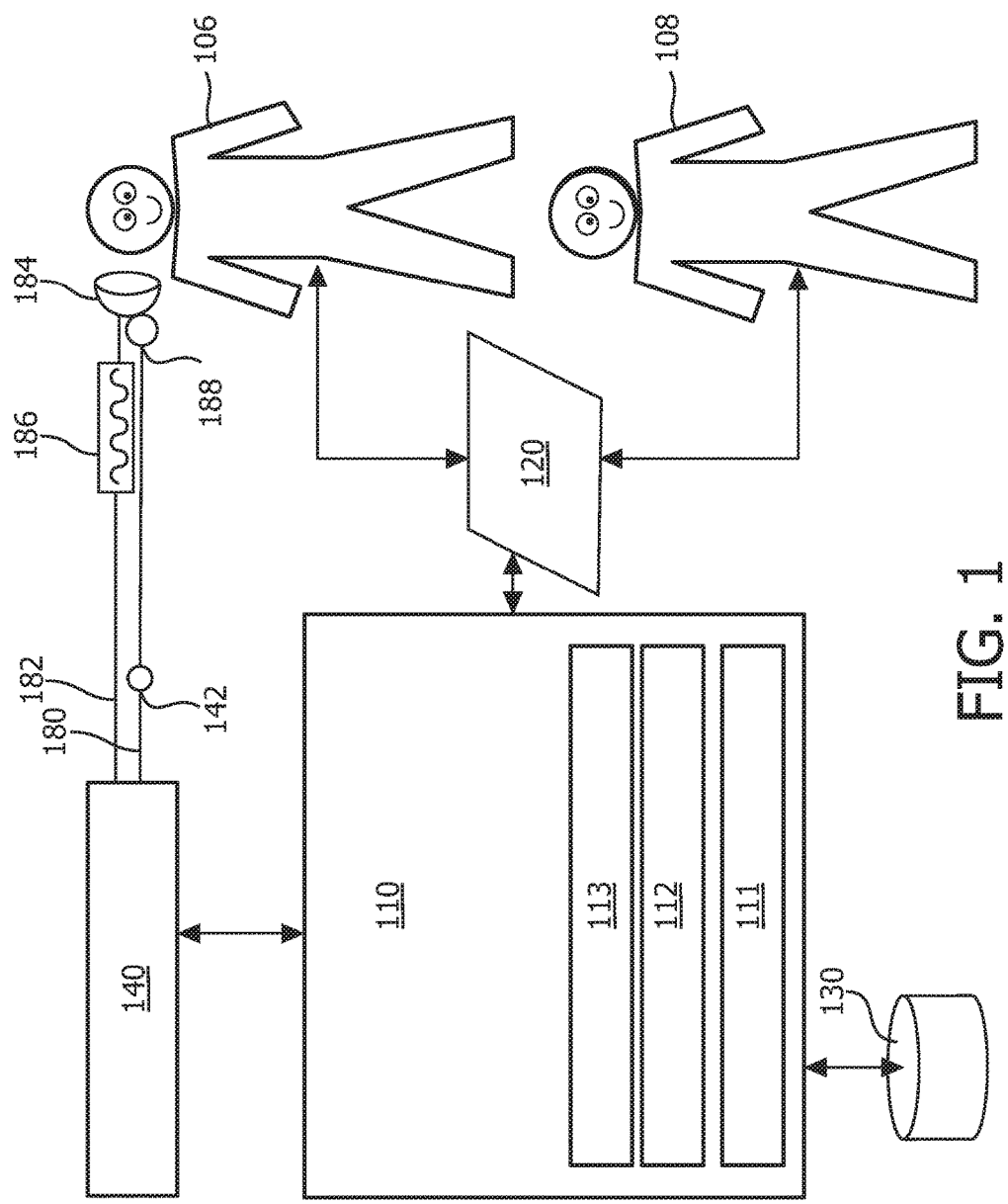
FIG. 1 schematically illustrates a system configured to treat sleep apnea while enhancing expiratory positive airway pressure according to certain embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to treat sleep apnea while enhancing expiratory positive airway pressure according to certain embodiments. Enhancing the expiratory positive airway pressure may include reducing the expiratory positive airway pressure. Reduction of the expiratory positive airway pressure may be with respect to a past expiratory positive airway pressure used in therapy for a given subject, and/or reduction with respect to the expiratory positive airway pressure implemented by conventional systems and/or techniques. A reduced level of expiratory positive airway pressure may be less intrusive, more comfortable, and/or provide other benefits over a relatively higher level of expiratory positive airway pressure. Other reasons for reducing the expiratory positive airway pressure are also contemplated.

To treat obstructive sleep apneas, a subject may benefit from the use of an expiratory positive airway pressure (EPAP) device. Providing an EPAP aims to prevent or open a collapsed and/or obstructed airway of the subject. A relatively low level of expiratory positive airway pressure that accomplishes this aim is sought, though the particular level may change throughout the subject's sleep. A measure for airway obstruction may be airway resistance, in particular upper airway resistance, which may be measured, calculated, or estimated based on parameters that are related to measurements taken by one or more sensors. Accordingly, in some embodiments, system 100 comprises a pressure generator 140, one or more sensors 142, a processor 110, a control module 111, a resistance module 112, an adjustment module 113, an infrasonic wave generator 186, and/or other components.

Pressure generator 140 may be integrated, combined, or connected with a positive airway pressure device (PAP/CPAP/BiPAP/etc.) and configured to provide a pressurized flow of breathable gas to the airway of subject 106, e.g. via subject interface 180. Pressure generator 140 may be configured to monitor and support the respiration of a subject, and adjust the expiratory positive airway pressure level, flow, and/or other parameters of the pressurized flow of breathable gas in substantial synchronization with the breathing cycle of the subject, e.g. when the subject is sleeping.

In some embodiments, respiratory support may be implemented as a higher and lower positive pressure of a (multi-level or bi-level) PAP device, respectively. For example, to support the airway during inspiration by subject 106, the pressure of the pressurized flow of breathable gas may be increased to an Inspiratory Positive Air Pressure (IPAP). Similarly, to support the airway during expiration by subject 106, the pressure of the pressurized flow of breathable gas may be decreased to an Expiratory Positive Air Pressure (EPAP). Other schemes for respiratory support through the delivery of a pressurized flow of breathable gas are contemplated. A PAP device may be configured such that one or more gas parameters of the pressurized flow of breathable gas are controlled in accordance with a therapeutic respiratory regimen for subject 106. The one or more gas parameters may include, for example, one or more of flow, pressure, temperature, humidity, aroma, velocity, acceleration, and/or other parameters. In certain embodiments, pressure generator 140 is part of an airway pressure device configured to provide types of therapy other than positive airway support therapy.

A pressurized flow of breathable gas may be delivered from pressure generator 140 to the airway of subject 106 by a subject interface 180. Subject interface 180 may include a conduit 182 and/or a subject interface appliance 184. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 may be configured to deliver the pressurized flow of breathable gas to the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

System 100 may include electronic storage 130 comprising electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more (breathing) parameters (as discussed elsewhere herein), information indicating whether the subject adequately complied with a therapy regimen, information indicating whether an apnea occurred, and/or other information. Electronic storage 130 may be a separate component within system 100, or electronic storage 130 may be provided integrally with one or more other components of system 100 (e.g., processor 110).

System 100 may include user interface 120 configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a report detailing the changes in expiratory positive airway pressure throughout a period during which the subject is sleeping. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to subject 106 by user interface 120 in the form of auditory signals, visual signals, tactile signals, and/or other sensory signals.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to subject 106 information related to breathing and/or the pressurized flow of breathable gas. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 may be configured to generate output signals conveying measurements related to parameters of respiratory airflow or airway mechanics, including one or more of flow, pressure, humidity, velocity, acceleration, and/or other parameters. Based on these parameters, a parameter determination module (and/or other components of system 100) may be configured to determine one or more parameters, including oscillatory flow generated from the vibrations in the upper airway, (tidal) volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, and/or other parameters. Measurements from sensor 142, or parameters based on these measurements, may be used to determine or estimate airway resistance, in particular upper airway resistance. Measurements from sensor 142 may be associated with specific timing within a breathing cycle or within the duration of the subject's sleep. For example, end pressure may be derived based on measurements taken at the end of an expiration when the flow at or near the flexible airway of the subject is at a reduced level, since flow affects airway resistance. Sensor 142 may be in fluid communication with conduit 182 and/or subject interface appliance 184.

The illustration of sensor 142 including a single member in FIG. 1 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the delivery of the gas to subject 106, and/or a respiratory effort by the subject. For example, a parameter may be related to a mechanical unit of measurement of a component of pressure generator 140 (or of a device that pressure generator 140 is integrated, combined, or connected with) such as rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a control module 111, a resistance module 112, an adjustment module 113, and/or other modules. Processor 110 may be configured to execute modules 111, 112, and/or 113 by software; hardware; firmware; some combination of software, hardware, and/or firmware; and/or other mechanisms for configuring processing capabilities on processor 110.

It should be appreciated that although modules 111, 112, and 113 are illustrated in FIG. 1 as being co-located within a single processing unit, in implementations in which processor 110 includes multiple processing units, one or more of modules 111, 112, and/or 113 may be located remotely from the other modules. The description of the functionality provided by the different modules 111, 112, and/or 113 described below is for illustrative purposes, and is not intended to be limiting, as any of modules 111, 112, and/or 113 may provide more or less functionality than is described. For example, one or more of modules 111, 112, and/or 113 may be eliminated, and some or all of its functionality may be provided by other ones of modules 111, 112, and/or 113. Note that processor 110 may be configured to execute one or more additional modules that may perform some or all of the functionality attributed below to one of modules 111, 112, and/or 113.

System 100 may comprise a parameter determination module configured to determine one or more parameters based on the output signals generated by sensor 142. The parameters may be related to airway resistance, in particular upper airway resistance. The one or more output signals may convey measurements related to breathing parameters and/or mechanical airway parameters of the subject. Parameters may include one or more of a tidal volume of the breathing of the subject, a respiratory rate, an inhalation time, an exhalation time, a flow rate of the breathing of the subject, and/or other parameters. Parameters may be related to and/or derived from measurements by sensor 142 of one or more gas parameters including (peak) flow, pressure, temperature, humidity, velocity, acceleration, gas composition (e.g. concentration(s) of one or more constituents), thermal energy dissipated, and/or other gas parameters of the pressurized flow of breathable gas. Parameters may be associated with specific timing within a breathing cycle or within the duration of the subject's sleep. In certain embodiments, a parameter may be related to and/or derived from a similar measurement as used to generate another parameter, though using a different specific timing within a breathing cycle or within the duration of the subject's sleep.

Control module 111 is configured to control pressure generator 140 in the provision of a pressurized flow of breathable gas delivered to the airway of subject 106 at a target expiratory positive airway pressure. As such, control module 111 may control aspects and/or settings of pressure generator 140 in order to adjust one or more parameters of the respiration of subject 106, particularly expiratory positive airway pressure. Application of the target expiratory positive airway pressure is intended to support the airway of subject 106 during expiration. This may include preventing a collapsed and/or obstructed airway of subject 106 during expiration. In the event that an airway collapse and/or obstruction could occur, the target expiratory positive airway pressure is intended to facilitate opening the collapsed and/or obstructed airway. The target expiratory positive airway pressure may change throughout the period during which the subject is sleeping, as a result of a change in body position of the subject, at the occurrence of an apnea, and/or for other reasons. The level of airway obstruction may be estimated, calculated, and/or measured by deriving the airway resistance of subject 106, in particular upper airway resistance.

Figure 2:
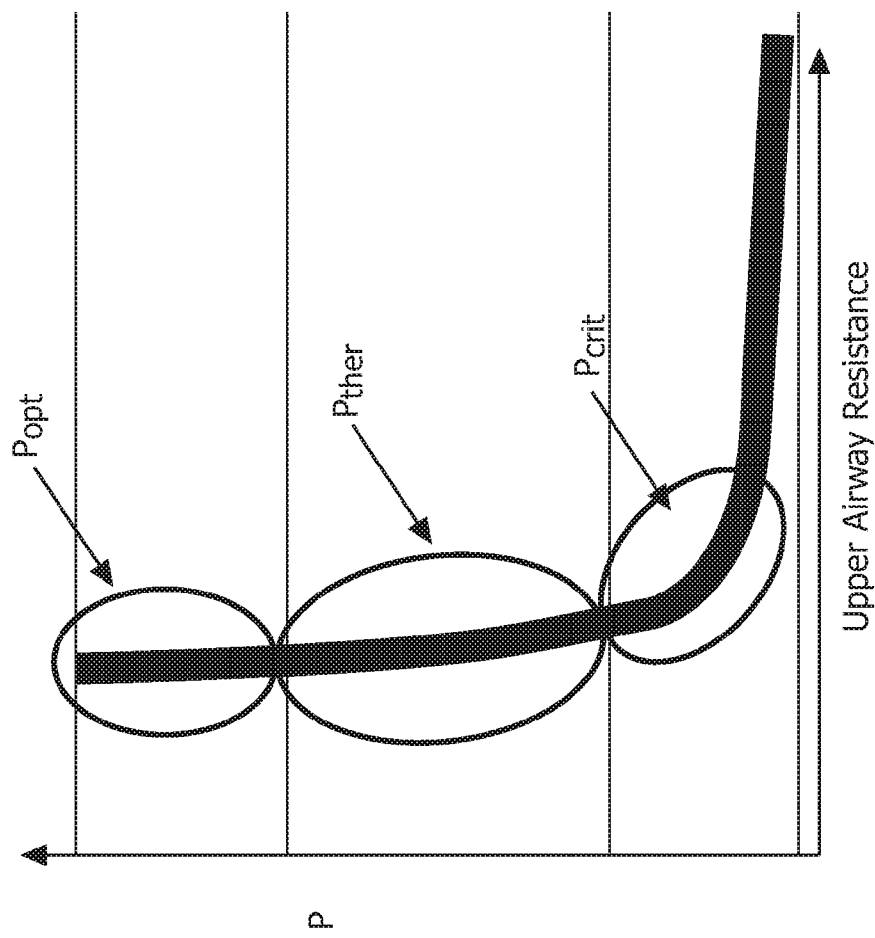
FIG. 2 illustrates the relationship between upper airway resistance and expiratory positive airway pressure.

Resistance module 112 is configured to estimate, calculate, and/or measure (upper) airway resistance of the subject based on one or more output signals from sensor 142. As airway resistance increases, the flow in relationship to the differential pressure across the airway decreases. By way of illustration, FIG. 2 illustrates the relationship between upper airway resistance and expiratory positive airway pressure. In the area labeled "Pcrit" the resistance sharply increases as the airway collapses. In the area labeled "Popt" the airway resistance barely decreases with increased pressure. The area labeled "Pther" is sought after for preventing airway collapse and having low airway resistance at a low level of expiratory positive airway pressure.

In certain embodiments, system 100 includes an infrasonic wave generator 186 and a wave sensor 188. Infrasonic wave generator 186 maybe configured to generate infrasonic waves at or near the airway of the subject. Wave sensor 188 is configured to generate one or more output signals conveying measurements related to a physiological response by the subject to the infrasonic waves. Infrasonic wave generator 186 may generate low frequency oscillations or pulses Infrasonic waves may have a frequency less than 20 Hz. (e.g. about 10 Hz or between about 5 Hz and about 15 Hz) that cause oscillations in the airway of the subject. Sensors may generate output signals conveying a measurement of the amplitude of pressure oscillations and flow oscillations, the ratio of which may be used to estimate upper airway resistance. For example, the amplitudes may be computed using a linear least squares method from the 10 Hz sensor signal. In certain embodiments, airway resistance may be estimated, calculated, and/or measured using a method including an interrupter method, a forced oscillation technique, signal analysis, image analysis, ultrasonic (no-flow) measurements, and/or other methods.

Adjustment module 113 is configured to adjust the target expiratory positive airway pressure based on the estimations of airway resistance, calculated, and/or measured (upper) airway resistance. The range of available levels of expiratory positive airway pressure may be delineated by a maximum expiratory positive airway pressure and/or a minimum expiratory positive airway pressure. Within this range, the adjustment module aims to determine a level of expiratory positive airway pressure based on the corresponding resistance. This may include selecting a level of expiratory positive airway pressure that corresponds to the lowest resistance available within the range, a level of expiratory positive airway pressure that corresponds to a resistance within a specific amount (percentage or actual amount) of the lowest resistance, and/or other selection techniques. The level of airway obstruction is in turn based on the level of (upper) airway resistance. A level of expiratory positive airway pressure that accomplishes a state exhibiting the lowest level of (upper) airway resistance (or a level of airway resistance sufficiently close to the lowest level of airway resistance) forms the moving target for adjustments made by adjustment module 113. For example, adjustment module 113 may establish the current level of airway resistance as a base resistance level which coincides with the current level of expiratory positive airway pressure.

In some embodiments, adjustment module 113 is configured to periodically adjust the target expiratory positive airway pressure upwards or downwards. Subsequently, adjustment module 113 may establish the new level of airway resistance which coincides with the new target level of expiratory positive airway pressure. Response to the new level of airway resistance being substantially lower than the base resistance level, the tentative adjustment is accepted. Substantially lower may mean at least about a 5% improvement, at least between about 5% and about 10% improvement, more than about 10% improvement, an absolute level of improvement expressed in the same units of measurement as the upper airway resistance, and/or another threshold of substantiality. Responsive to the new level of airway resistance being not substantially lower than the base resistance level, the tentative adjustment may be rejected and/or reversed for an upward adjustment of expiratory positive airway pressure, or accepted for a downward adjustment of expiratory positive airway pressure. Adjustment module 113 may update or reestablish the base resistance level in preparation for a subsequent adjustment. Adjustments may alternate between upwards adjustments and downwards adjustments in a continual and proactive search for the lowest target expiratory positive airway pressure coinciding with the lowest level of (upper) airway resistance, during the subject's sleep.

Figure 3:
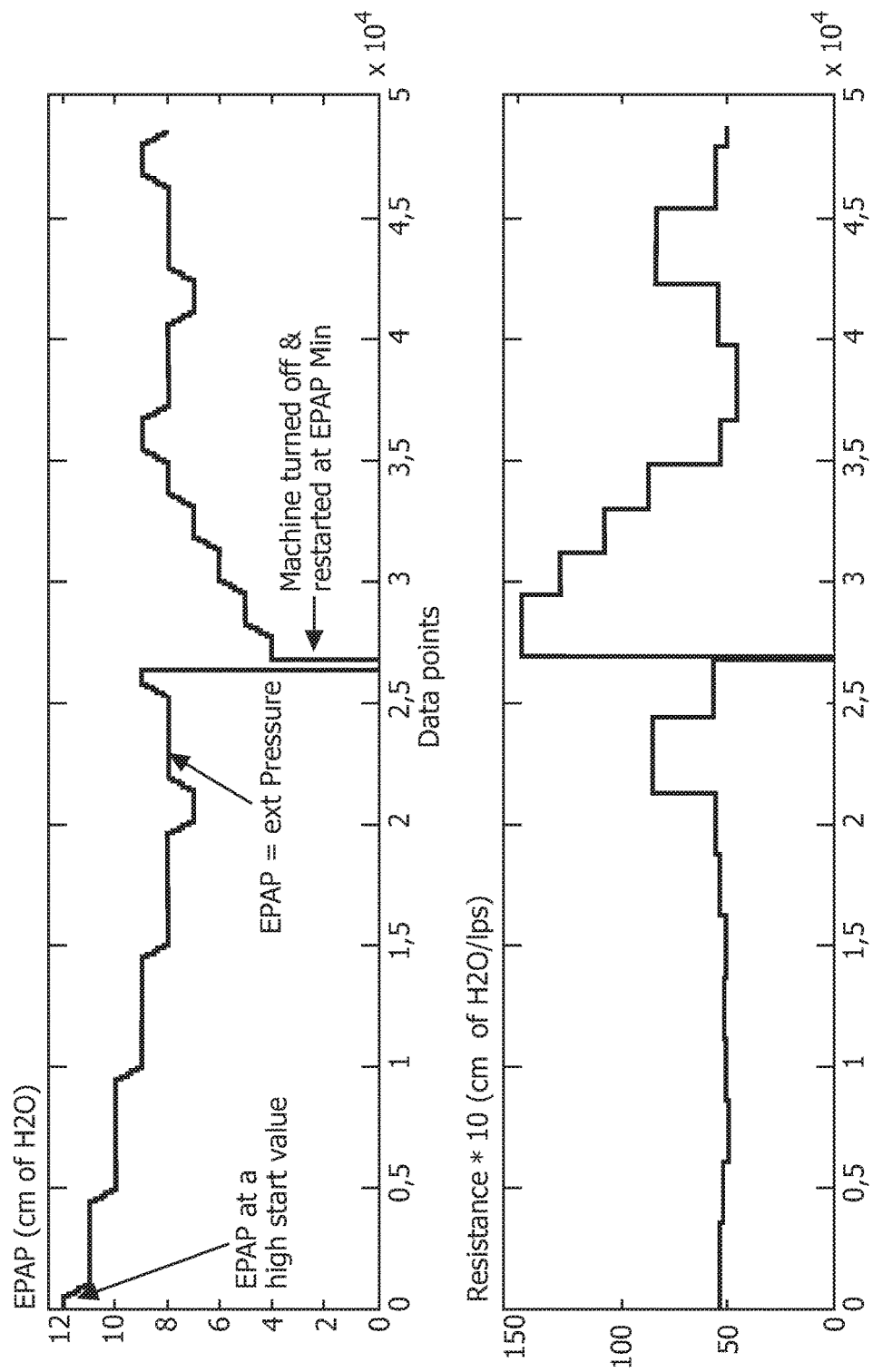
FIG. 3 illustrates adjustments of EPAP level according to certain embodiments.

By way of illustration, FIG. 3 illustrates adjustments of EPAP level according to certain embodiments, for two tests. The top area of FIG. 3 shows the varying levels of EPAP (on the Y-axis) in relation to a duration as depicted by data points (on the X-axis). A data point may relate to a fixed number of breaths by the subject. The bottom area of FIG. 3 shows the associated levels of upper airway resistance. The first half of the figure illustrates the first test, in which EPAP is adjusted downward until a target expiratory positive airway pressure of 8 cm of H2O is found. The downward adjustment at 2×104 data points is reversed at the first opportunity, since the associated level of airway resistance sharply increases. The second half of the figure illustrates the second test, in which EPAP is adjusted upwards until the target expiratory positive airway pressure is found. The tentative upward adjustment at 3.5×104 data points is reversed at the first opportunity, due to an increased level of airway resistance. Similarly, the tentative downward adjustment at 4×104 data points is reversed.

Figure 4:
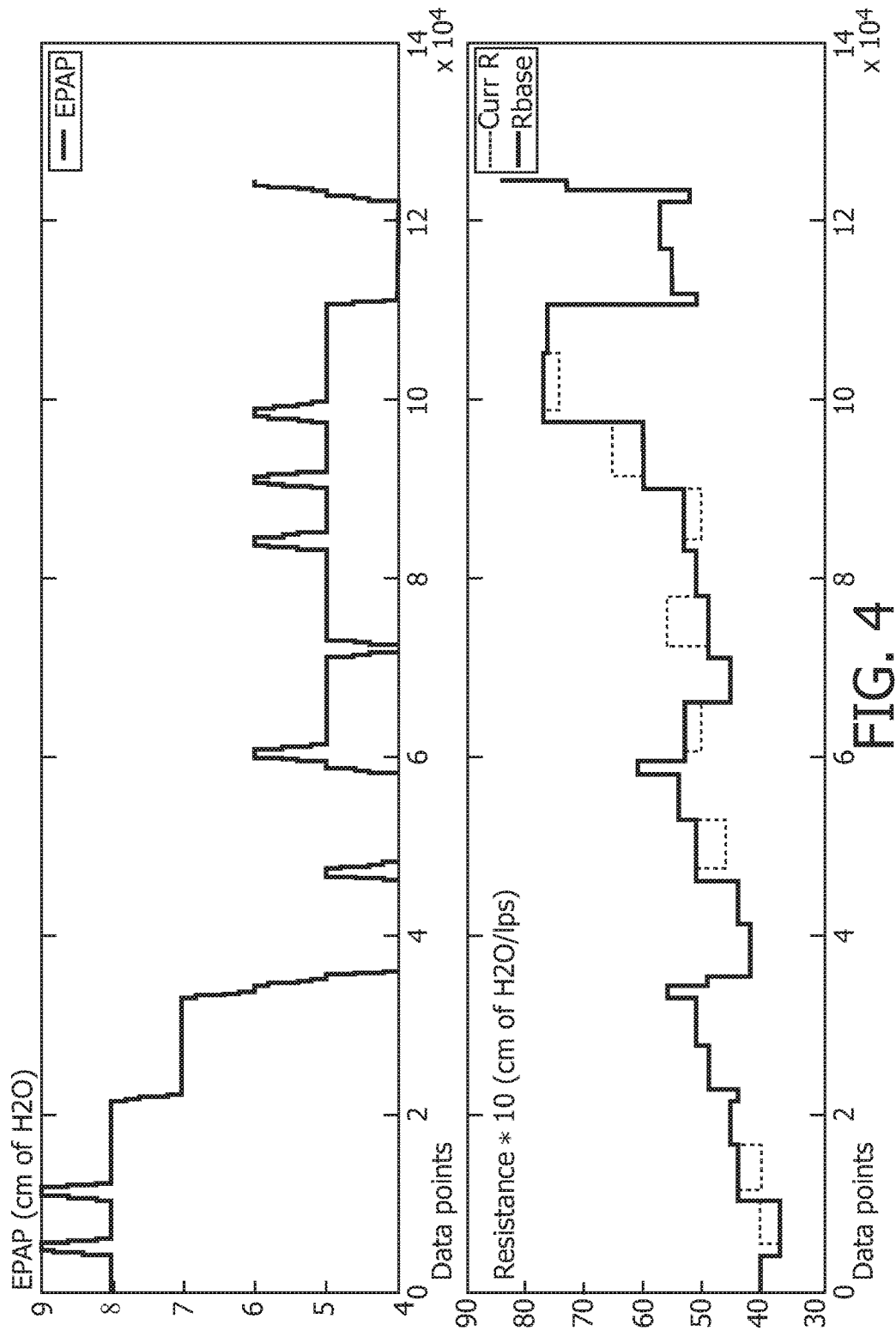
FIG. 4 illustrates adjustments of EPAP level according to certain embodiments.

By way of illustration, FIG. 4 illustrates adjustments of EPAP level according to certain embodiments, for a longer test in which the target expiratory positive airway pressure changes, e.g. due to the body position of the subject.

Treating obstructive sleep apnea according to the methods and systems described herein ignores central apneas, responds timely to changes in airway resistance, and avoids practical limitations of certain methods of determining EPAP levels, including Inspiratory Flow Limitation (IFL). Such limitations include cases where high Inspiratory pressure stints an airway open and no IFL is observed, irregular breathing, and/or changes in leak estimation or glottis closures.

Figure 5:
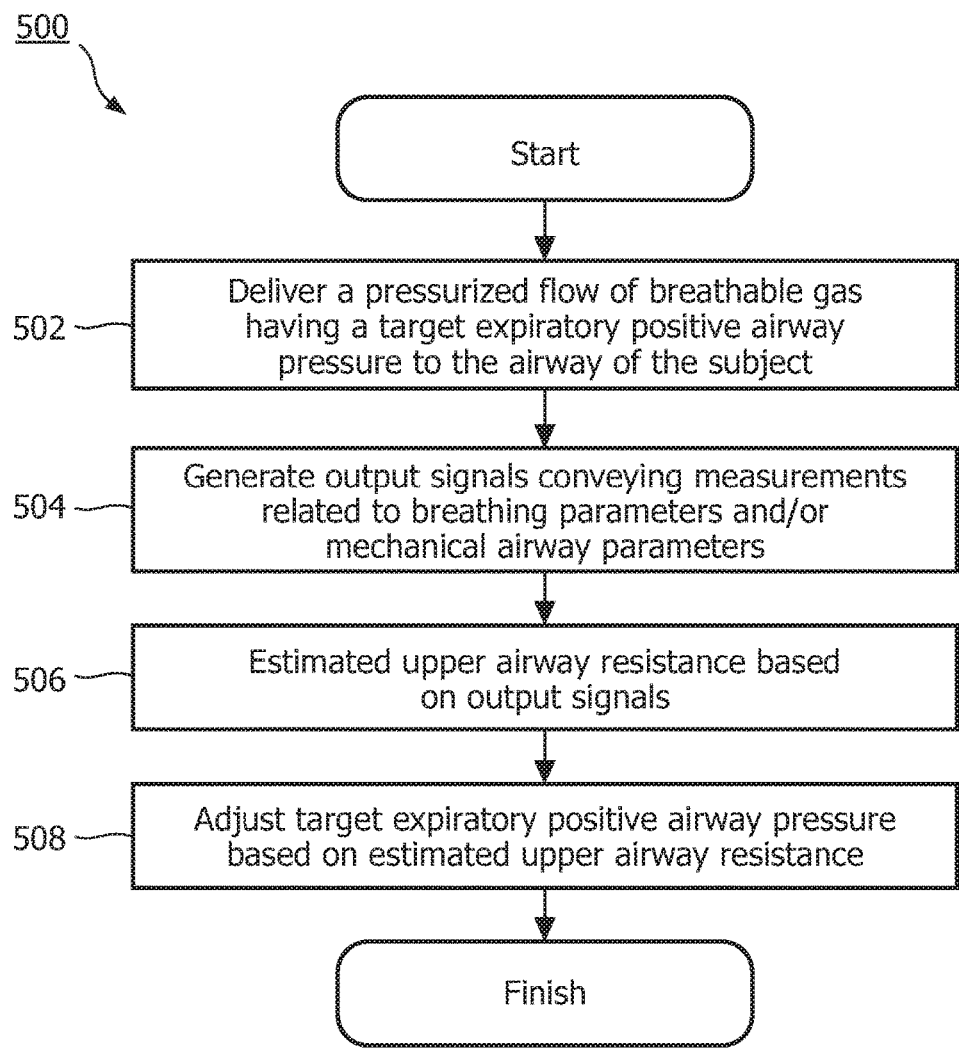
FIG. 5 illustrates a method for treating sleep apnea while enhancing expiratory positive airway pressure according to certain embodiments.

FIG. 5 illustrates a method 500 for treating obstructive sleep apnea of a subject. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a pressurized flow of breathable gas having a target expiratory positive airway pressure is delivered to the airway of a subject. In one embodiment, operation 502 is performed by a pressure generator similar to or substantially the same as pressure generator 140 (shown in FIG. 1 and described above).

At an operation 504, output signals conveying measurements related to breathing parameters and/or mechanical airway parameters are generated. In one embodiment, operation 504 is performed by a sensor similar to or substantially the same as sensor 142 (shown in FIG. 1 and described above).

At an operation 506, the upper airway resistance of the subject is estimated, calculated, and/or measured based on the output signals. In one embodiment, operation 506 is performed by a resistance module similar to or substantially the same as resistance module 112 (shown in FIG. 1 and described above).

At an operation 508, the target expiratory positive airway pressure is adjusted based on the estimations of airway resistance and/or calculated and/or measured upper airway resistance. In one embodiment, operation 508 is performed by an adjustment module similar to or substantially the same as adjustment module 113 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for treating sleep apnea of a subject having an airway by enhancing expiratory positive airway pressure, the system comprising:
    (a) a pressure generator configured to generate a pressurized flow of breathable gas for delivery to the airway of the subject,
    (b) one or more sensors configured to generate one or more output signals conveying measurements related to one or more parameters of the subject; and
    (c) one or more processors configured to execute computer program modules, the computer program modules comprising:
        (1) a control module configured to control the pressure generator to adjust one or more parameters of the pressurized flow of the breathable gas such as that the airway of the subject is provided with an inspiratory positive airway pressure during inhalation and a target expiratory positive airway pressure during exhalation of the subject, the inspiratory positive airway pressure being greater than the target expiratory positive airway pressure,
        (2) a resistance module configured to estimate upper airway resistance of the subject based on the one or more output signals, and
        (3) and adjustment module configured to periodically adjust the target expiratory positive airway pressure based on the estimated upper airway resistance, and to determine whether to reverse or accept an individual periodical adjustment based on subsequently estimated upper airway resistance such that the target expiratory positive airway pressure forms a moving target expiratory positive airway pressure comprising a level of expiratory positive airway pressure that facilitates a reduced amount of upper airway resistance, wherein the adjustment module is configured to determine whether to reverse or accept the individual periodical adjustment of the target expiratory positive airway pressure by comparing a change in estimated upper airway resistance with a threshold.

2. The system of claim 1, further comprising an infrasonic wave generator configured to generate infrasonic pressure oscillations at or near the airway of the subject, wherein one or more output signals conveying measurements are further related to a physiological response by the subject to the infrasonic pressure oscillations, wherein the physiologic response includes flow oscillations, and wherein estimation by the resistance module is further based on a ratio of an amplitude of the pressure oscillations and an amplitude of the flow oscillations.

3. The system of claim 1, wherein the threshold for change in estimated upper airway resistance is a percentage of the estimated upper airway resistance.

4. A method of treating sleep apnea of a subject having an airway by enhancing expiratory positive airway pressure, the method comprising;
   delivering, with a pressure generator, a pressurized flow of breathable gas having an inspiratory positive airway pressure during inhalation and a target expiratory positive airway pressure during exhalation to the airway of the subject, the inspiratory positive airway pressure being greater than the target expiratory positive airway pressure;
   generating one or more output signals conveying measurements related to one or more parameters of the subject;
   estimating upper airway resistance of the subject based on the one or more output signals;
   periodically adjusting the target expiratory positive airway pressure based on the estimated upper airway resistance; and
   determining, with a processor, whether to reverse or accept an individual periodical adjustment based on subsequently estimated upper airway resistance such that the target expiratory positive airway pressure forms a moving target expiratory positive airway pressure comprising a level of expiratory positive airway pressure that facilitates a reduced amount of upper airway resistance, wherein determining whether to reverse or accept the individual periodical adjustment of the target expiratory positive airway pressure includes comparing a change in estimated upper airway resistance with a threshold.

5. The method of claim 4, further comprising:
   generating infrasonic pressure oscillations at or near the airway of the subject, wherein one or more output signals conveying measurements are further related to a physiological response by the subject to the infrasonic pressure oscillations, wherein the physiologic response includes flow oscillations, and wherein estimating the upper airway resistance of the subject is further based on a ratio of an amplitude of the pressure oscillations and an amplitude of the flow oscillations.

6. The method of claim 4, wherein the threshold for change in estimated upper airway resistance is a percentage of the estimated upper airway resistance.

7. A system configured to treat sleep apnea of a subject having an airway by enhancing expiratory positive airway pressure, the system comprising:
   means for delivering a pressurized flow of breathable gas having an inspiratory positive airway pressure during inhalation and a target expiratory positive airway pressure during exhalation to the airway of a subject, the inspiratory positive airway pressure being greater than the target expiratory positive airway pressure;
   means for generating one or more output signals conveying measurements related to one or more parameters of the subject;
   means for estimating upper airway resistance of the subject based on the one or more output signals;
   means for periodically adjusting the target expiratory positive airway pressure based on the estimated upper airway resistance; and
   means for determining whether to reverse or accept an individual periodical adjustment based on subsequently estimated upper airway resistance such that the target expiratory positive airway pressure forms a moving target expiratory positive airway pressure comprising a level of expiratory positive airway pressure that facilitates a reduced amount of upper airway resistance, wherein the means for determining whether to reverse or accept the individual periodical adjustment of the target expiratory positive airway pressure is configured to compare a change in estimated upper airway resistance with a threshold.

8. The system of claim 7, further comprising:
   means for generating infrasonic pressure oscillations at or near the airway of the subject, wherein one or more output signals convey measurements related to a physiological response by the subject to the infrasonic pressure oscillations, wherein the physiologic response includes flow oscillations, and wherein estimation by the means for estimating is based on a ratio of an amplitude of the pressure oscillations and an amplitude of the flow oscillations.

9. The system of claim 7, wherein the threshold for change in estimated upper airway resistance is a percentage of the estimated upper airway resistance.

* * * * *